(12) United States Patent
Chang et al.

(10) Patent No.: US 11,360,082 B2
(45) Date of Patent: Jun. 14, 2022

(54) DETECTION KIT AND METHOD FOR DETECTING ABUSED DRUGS

(71) Applicant: National Taiwan University, Taipei (TW)

(72) Inventors: Huan-Tsung Chang, Taipei (TW); Yao-Te Yen, Taipei (TW); Yu-Shen Lin, Taipei (TW); Yu-Syuan Lin, Taipei (TW)

(73) Assignee: National Taiwan University, Taipei (TW)

( * ) Notice: Subject to any disclaimer, the term of this patent is extended or adjusted under 35 U.S.C. 154(b) by 331 days.

(21) Appl. No.: 16/439,664

(22) Filed: Jun. 12, 2019

(65) Prior Publication Data
US 2020/0225216 A1 Jul. 16, 2020

(30) Foreign Application Priority Data

Jan. 10, 2019 (TW) .................. 108101059

(51) Int. Cl.
| | | |
|---|---|---|
| *G01N 33/542* | (2006.01) | |
| *G01N 21/51* | (2006.01) | |
| *G01N 33/94* | (2006.01) | |
| *G01N 33/533* | (2006.01) | |
| *G01N 21/64* | (2006.01) | |
| *G01N 21/59* | (2006.01) | |

(52) U.S. Cl.
CPC .......... *G01N 33/542* (2013.01); *G01N 21/51* (2013.01); *G01N 21/59* (2013.01); *G01N 21/6428* (2013.01); *G01N 33/533* (2013.01); *G01N 33/94* (2013.01)

(58) Field of Classification Search
None
See application file for complete search history.

(56) References Cited

U.S. PATENT DOCUMENTS 10,041,962 B1 8/2018 Chang et al.

FOREIGN PATENT DOCUMENTS

| CN | 105181955 | 4/2017 |
| CN | 107860758 | 3/2018 |
| CN | 109054822 | 12/2018 |
| TW | 201621317 | 6/2016 |
| TW | 1571634 | 2/2017 |
| WO | 2018154078 | 8/2018 |

OTHER PUBLICATIONS

Jun Zuo et al., "Preparation and Application of Fluorescent Carbon Dots", Journal of Nanomaterials vol. 2015, Article ID 787862, 13 pages, Jun. 21, 2015, pp. 1-14.
"Office Action of Taiwan Counterpart Application," dated Aug. 8, 2019, p. 1-p. 7.

*Primary Examiner* — Xiaoyun R Xu
(74) *Attorney, Agent, or Firm* — JCIPRNET (57) ABSTRACT

A detection kit is suitable for detecting a target compound. The detection kit includes a reaction container, an inspection solution composed of a hydrophobic solvent, and a plurality of fluorescent materials. The inspection solution is disposed in the reaction container. The fluorescent materials are dispersed in the inspection solution. The fluorescent material emits fluorescence, and after the fluorescent materials interact with the target compound, the intensity of the fluorescence emitted by the fluorescent materials is reduced.

6 Claims, 7 Drawing Sheets

DETECTION KIT AND METHOD FOR DETECTING ABUSED DRUGS

CROSS-REFERENCE TO RELATED APPLICATION

This application claims the priority benefit of Taiwan application serial no. 108101059, filed on Jan. 10, 2019. The entirety of the above-mentioned patent application is hereby incorporated by reference herein and made a part of this specification.

BACKGROUND OF THE INVENTION

Field of the Invention

The invention relates to a detection kit, and more particularly, to a detection kit for detecting abused drugs and a method for detecting abused drugs using the detection kit.

Description of Related Art

The manufacturing principle of today's commercial rapid screening test strips/reagents for abused drugs are based on immunoassay. After abused drugs interact with antibodies on test strips/reagents, the dye molecules released from the antibodies may be colored and detected. Although the use of immunoassay test strips/reagents has the advantage of high specificity, the use of immunoassay rapid screening test strips/reagents for abused drugs still has its disadvantages. For example, the production of antibodies on test strips/reagents needs to be obtained through animal experiments. The method is less humane, and the physiological states of the batches of animals all affect the quality of the antibodies, so the difference between the batches of antibodies produced is greater. In other words, today's commercial rapid screening test strips/reagents for abused drugs have the disadvantages of difficult production of antibodies, high cost, short lifespan, and difficult storage. Therefore, there is an urgent need for a detection method that may solve the above disadvantages.

SUMMARY OF THE INVENTION

The invention provides a detection kit and a method for detecting abused drugs that have the advantages such as simple manufacture, low cost, high stability, and easy storage.

The detection kit of the invention is suitable for detecting a target compound. The detection kit includes a reaction container, and an inspection solution composed of a hydrophobic solvent, and a plurality of fluorescent materials. The inspection solution is disposed in the reaction container. The fluorescent materials are dispersed in the inspection solution. The fluorescent materials emit fluorescence, and after the fluorescent materials interact with the target compound, an intensity of the fluorescence emitted by the fluorescent materials is decreasing.

In an embodiment of the invention, the above hydrophobic solvent includes toluene, benzene, xylene, ethyl acetate, dichloromethane, or trichloromethane.

In an embodiment of the invention, the fluorescent materials are carbon quantum dots and are synthesized from a hydrophobic precursor.

In an embodiment of the invention, the fluorescent materials emit the fluorescence after being excited by an ultraviolet light, and after the fluorescent materials interact with the target compound, the intensity of the fluorescence emitted by the fluorescent materials is reduced.

In an embodiment of the invention, the above target compound includes nimetazepam, flunitrazepam, nitrazepam, clonazepam, and nitro-substituted benzodiazepines.

The method for detecting abused drugs of the invention includes the following steps. The above detection kit is provided. The test liquid is added to the reaction container of the detection kit. The test liquid is thoroughly mixed with the inspection solution and allowed to stand. The inspection solution is irradiated with an ultraviolet light source after the test liquid is thoroughly mixed and reacted with the inspection solution. The reducing condition of the fluorescent intensity of the fluorescent materials in the inspection solution is determined under ultraviolet light source irradiation to confirm whether the test liquid has an abused drug. The concentration of abused drug in the test liquid is determined according to the reducing condition.

In an embodiment of the invention, the method for detecting abused drugs above further includes the following steps. When the test liquid is added to the reaction container of the detection kit, the test liquid is slowly added to the inspection solution; or after the test liquid is added to the reaction container of the detection kit, the reaction container is evenly shaken up and down to increase the interaction between the abused drug in the test liquid and the fluorescent materials in the inspection solution. In particular, when the test liquid has the abused drug, the abused drug in the test liquid causes the fluorescence of the fluorescent materials in the inspection solution to be reduced.

In an embodiment of the invention, the method for confirming the concentration of the abused drug in the test liquid according to the reducing condition includes the following steps. A series of the abused drug of known concentration is provided in the reaction container of the detection kit. Irradiation is performed with an ultraviolet light source after the abused drug interacts with the fluorescent materials in the inspection solution. A fluorescence intensity of the abused drug at each concentration is determined to establish a standard concentration versus relative fluorescence quenching curve. The reducing condition is determined based on the standard concentration versus relative fluorescence quenching curve to confirm the concentration of the abused drug in the test liquid.

Based on the above, in the detection kit and the method for detecting abused drugs of the invention, the detection kit includes a reaction container, and an inspection solution composed of a hydrophobic solvent, and a plurality of fluorescent materials. In particular, the inspection solution is disposed in the reaction container and the fluorescent materials are dispersed in the inspection solution. Next, the test liquid is added to the reaction container and thoroughly mixed with the inspection solution and allowed to stand. Then, after the test liquid is thoroughly mixed and reacted with the inspection solution, the reducing condition of the fluorescence of the fluorescent materials in the inspection solution may be determined under ultraviolet light source irradiation to confirm whether the test liquid has abused drugs. Via this design, the detection kit and the method for detecting abused drugs of the invention have advantages such as simple manufacture, low cost, high stability, and easy storage.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
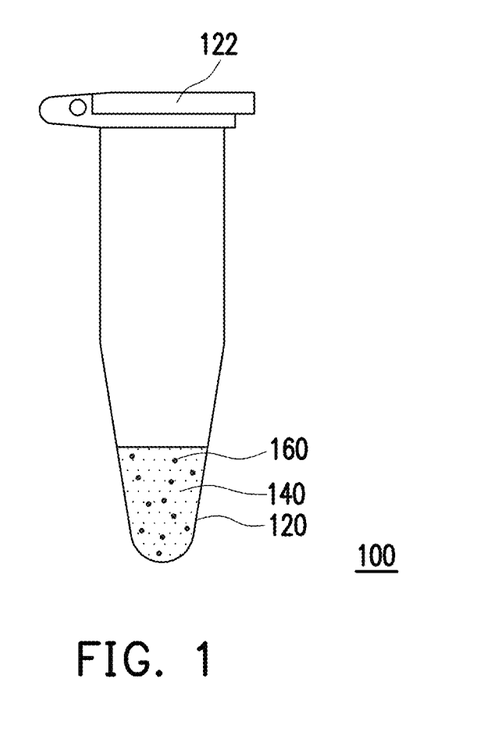
FIG. 1 is a schematic of a detection kit of an embodiment of the invention.

FIG. 1 is a schematic of a detection kit of an embodiment of the invention. Referring to FIG. 1, a detection kit 100 of the present embodiment is suitable for detecting a target compound, and the target compound is, for example, a drug such as nimetazepam, flunitrazepam, nitrazepam, clonazepam and nitro-substituted benzodiazepine-type sleeping rape compound drug having a related structure, but is not limited thereto.

In the present embodiment, the detection kit 100 includes a reaction container 120, an inspection solution 140 composed of a hydrophobic solvent, and a plurality of fluorescent materials 160. In particular, the inspection solution 140 is disposed in the reaction container 120 and the fluorescent materials 160 are dispersed in the inspection solution 140. In the present embodiment, the hydrophobic solvent is, for example, toluene, benzene, xylene, ethyl acetate, dichloromethane, trichloromethane, or other suitable organic solvents, but is not limited thereto. In the present embodiment, the fluorescent materials 160 emit fluorescence, and after the fluorescent materials 160 interact with the target compound, the intensity of the fluorescence emitted by the fluorescent materials 160 is reduced.

In detail, the fluorescent materials 160 of the present embodiment are, for example, carbon quantum dots synthesized from the hydrophobic precursor phenylalanine, but is not limited thereto. In other embodiments, the fluorescent materials 160 only need to be materials capable of emitting fluorescence.

In the present embodiment, the carbon quantum dots used as the fluorescent materials 160 are at least suitable for detecting abused drugs such as nimetazepam, flunitrazepam, nitrazepam, clonazepam or a nitro-substituted benzodiazepine-type sleeping rape compound drug having a related structure. Specifically, when the fluorescent materials 160 are carbon quantum dots, the fluorescent materials 160 may be excited by ultraviolet light and emit blue fluorescence, and after the fluorescent materials 160 interact with a target compound, the intensity of blue fluorescence emitted by the fluorescent materials 160 is reduced, such that the presence of abused drugs may be determined.

The following describes a method of using the above detection kit 100 to detect abused drugs.

Figure 2A:
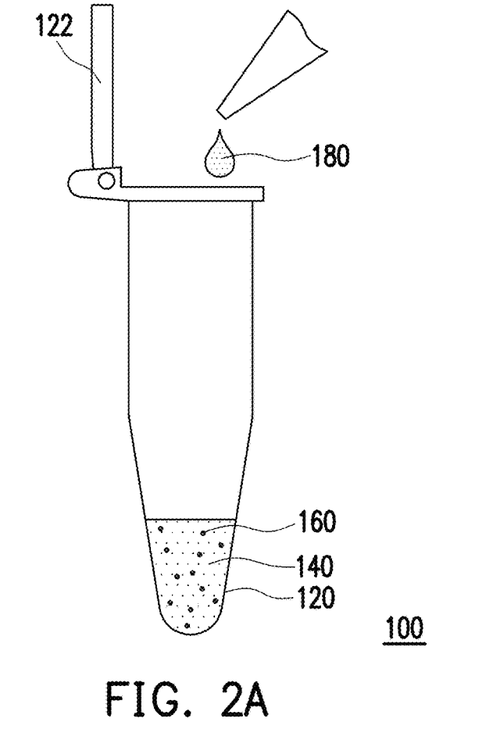
FIG. 2A to FIG. 2B show a method flowchart for detecting abused drugs using a detection kit in an embodiment of the invention.
Figure 2B:
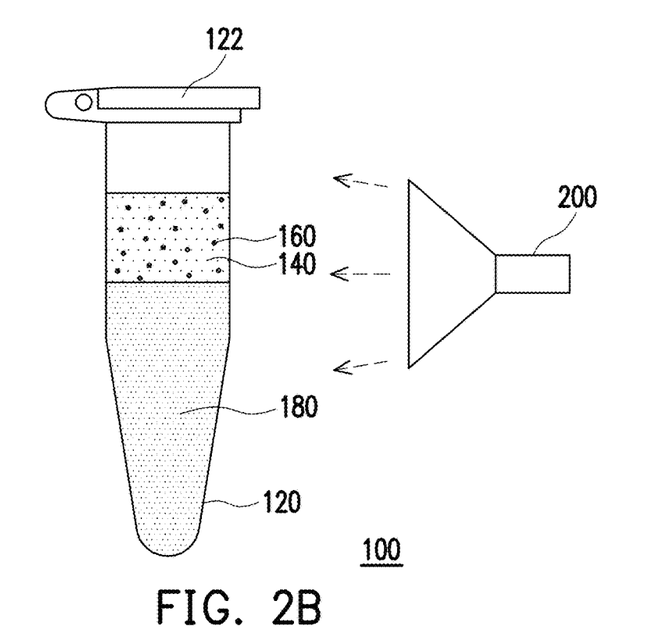

FIG. 2A to FIG. 2B show a method flowchart for detecting abused drugs using a detection kit in an embodiment of the invention. Referring to FIG. 2A, the detection kit 100 as shown in FIG. 1 is provided, wherein the inspection solution 140 is disposed in the reaction container 120, and the fluorescent materials 160 are dispersed in the hydrophobic solvent 120. Next, a top cover 122 of the reaction container 120 is opened, and a test liquid 180 is added to the reaction container 120 of the detection kit 100. In the present embodiment, the test liquid 180 is hydrophilic, and the test liquid 180 is, for example, beer, red wine, orange juice, whiskey, or other hydrophilic test liquids, but is not limited thereto. Then, referring to FIG. 2B, the top cover 122 is closed, and the test liquid 180 is thoroughly mixed with the inspection solution 120 and left to stand for several minutes.

Specifically, when abused drugs are present in the test liquid 180, the abused drugs in the test liquid 180 interact with the fluorescent materials 160 in the inspection solution 140, so that the abused drugs may reduce the fluorescence intensity of the fluorescent materials 160 in the inspection solution 140. Then, after the interaction, irradiation is performed via an ultraviolet light source 200. Under the irradiation of the ultraviolet light source 200, the decreasing of the fluorescent intensity of the fluorescent materials 160 in the inspection solution 140 is determined to confirm whether the test liquid 180 has abused drugs and to confirm the concentration of the abused drugs in the test liquid 180 according to the quenching ratio.

It should be noted that, in the present embodiment, when the test liquid 180 is added to the reaction container 120 of the detection kit 100, the test liquid 180 may be slowly added to the inspection solution 140 to improve the interaction between the abused drugs in the test liquid 180 and the fluorescent materials 160 in the inspection solution 140, but the invention is not limited thereto. In some embodiments, after the test liquid 180 is added to the reaction container 120 of the detection kit 100, the reaction container 120 may be evenly shaken up and down to increase the interaction between the abused drugs in the test liquid 180 and the fluorescent materials 160 in the inspection solution 140.

In the present embodiment, the method for confirming the concentration of the abused drugs in the test liquid 180 according to the reducing condition includes the following steps. First, a series of the abused drugs of known concentrations is provided in the reaction container 120 of the detection kit 100. Irradiation is performed with the ultraviolet light source 200 after the abused drugs interact with the fluorescent materials 160 in the inspection solution 140. A fluorescence intensity of the abused drugs at each concentration is determined to establish a standard concentration versus relative fluorescence quenching curve. The reducing condition is determined based on the standard concentration versus relative fluorescence quenching curve to confirm the concentration of the abused drugs in the test liquid 180. Therefore, via this method, the quantification of abused drug concentrations may be performed based on the reducing condition of the fluorescence.

EXPERIMENTAL EXAMPLES

In order to make the method for detecting abused drugs using the detection kit 100 of the invention easier to understand, the following experimental examples are provided.

Experimental Example A

In this experimental example, carbon quantum dots are used as the fluorescent materials 160, and the abused drugs to be detected include nimetazepam, flunitrazepam, clonazepam, nitrazepam or a nitro-substituted benzodiazepine-type sleeping rape compounding drug having a related structure. In this experimental example, the effect of nimetazepam or flunitrazepam on the fluorescence intensity of carbon quantum dots in the inspection solution 140 is determined. In this experimental example, the carbon quantum dots were prepared by placing 2.0 g of D-phenylalanine in 30 ml of toluene and then reacting in an oven at 240° C. for 14 hours. The reacted liquid was cooled to room temperature (25° C.) and filtered via a 0.22 μm polytetrafluoroethylene membrane to obtain a dark brown liquid. Then, a mixed solution of methanol and ultrapure water (30 ml, v/v=1:1) was used to remove impurities, and drying was performed to obtain a pure carbon quantum dot powder. Next, the pure carbon quantum dot powder was dispersed in 30 ml of toluene to prepare a carbon quantum dot solution having a concentration of about 15.76 mg/ml, and the following experiment was performed.

It is worth noting that since the fluorescent materials of this experimental example are chemically synthesized, their quality may be monitored to achieve high stability between batches. In addition, the fluorescent materials of this experimental example may be synthesized from organic matter, and even organic waste may be used as a synthetic precursor of the invention, thereby conforming to the field of green chemistry.

Figure 3A:
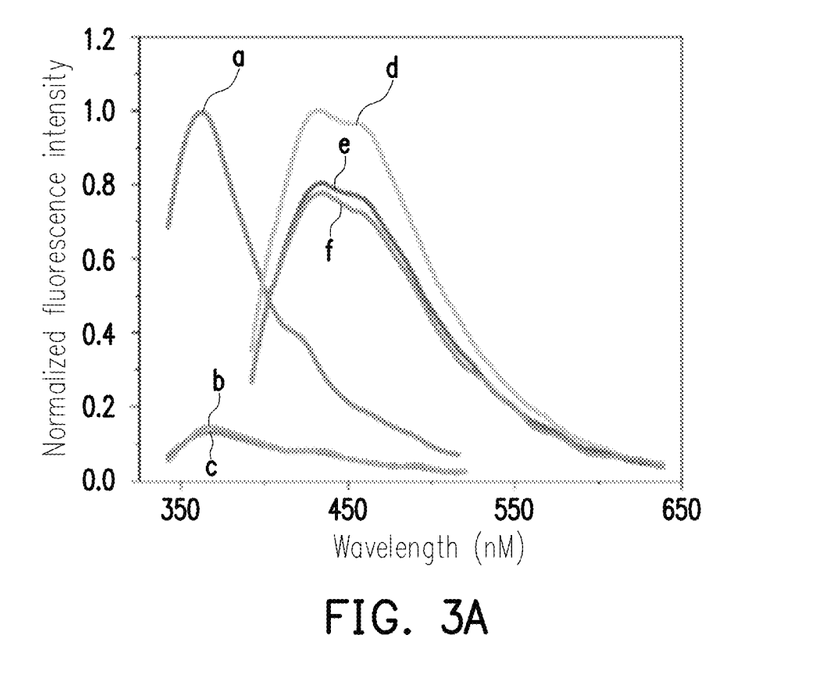
FIG. 3A shows a fluorescence emission spectrum under ultraviolet light irradiation at 300 nm or 365 nm after the detection kit of an embodiment of the invention interacts with nimetazepam, lunitrazepam, nitrazepam, and clonazepam.
Figure 3B:
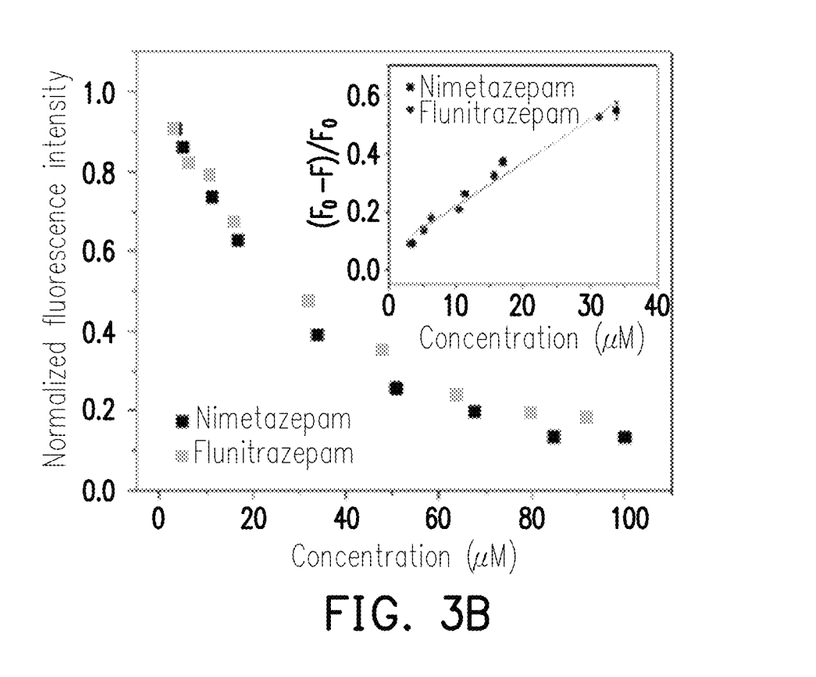
FIG. 3B shows a standard concentration versus relative fluorescence intensity curve established under ultraviolet light irradiation at 300 nm after the detection kit of an embodiment of the invention interacts with different concentrations of nimetazepam or flunitrazepam and a standard concentration versus relative fluorescence quenching curve (embedded figure).
Figure 3C:
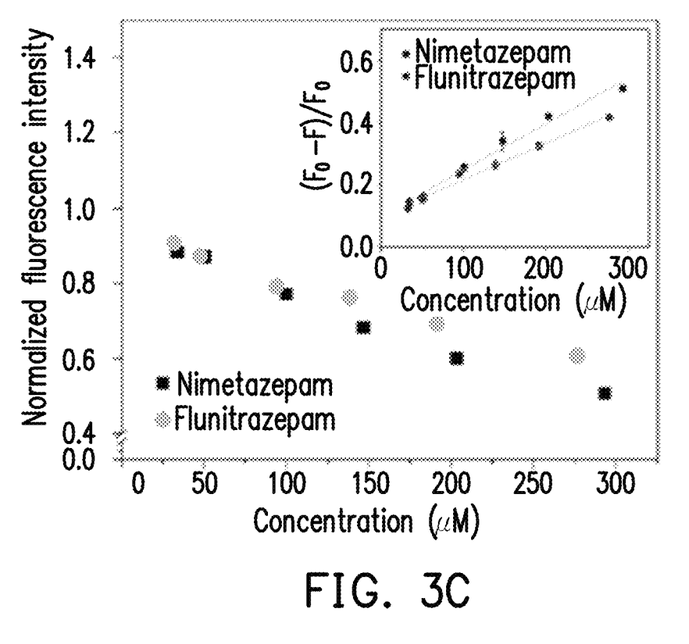
FIG. 3C shows a standard concentration versus relative fluorescence intensity curve established under ultraviolet light irradiation at 365 nm after the detection kit of an embodiment of the invention interacts with different concentrations of nimetazepam or flunitrazepam and a standard concentration versus relative fluorescence quenching curve (embedded figure).

FIG. 3A shows a fluorescence emission spectrum under ultraviolet light irradiation at 300 nm or 365 nm after the detection kit of an embodiment of the invention interacts with nimetazepam, flunitrazepam, nitrazepam, and clonazepam. FIG. 3B shows a standard concentration versus relative fluorescence intensity curve established under ultraviolet light irradiation at 300 nm after the detection kit of an embodiment of the invention interacts with different concentrations of nimetazepam or flunitrazepam and a standard concentration versus relative fluorescence quenching curve (embedded figure). FIG. 3C shows a standard concentration versus relative fluorescence intensity curve established under ultraviolet light irradiation at 365 nm after the detection kit of an embodiment of the invention interacts with different concentrations of nimetazepam or flunitrazepam and a standard concentration versus relative fluorescence quenching curve (embedded figure).

Please refer first to FIG. 3A comparing the fluorescence emission spectrum under irradiation by ultraviolet light at 300 nm or 365 nm respectively after the carbon quantum dot solution interacts with 0 μM of nimetazepam or flunitrazepam, after the carbon quantum dot solution interacts with 100 μM of nimetazepam, and after the carbon quantum dot solution interacts with 100 μM of flunitrazepam. In particular, the carbon quantum dot solution in the reaction container is about 0.5 ml, and the nimetazepam or flunitrazepam test solution is about 1.5 ml. FIG. 3A shows a fluorescence emission spectrum under ultraviolet light irradiation at 300 nm (spectrum a) or a fluorescence emission spectrum under ultraviolet light irradiation at 365 nm (spectrum d) after the carbon quantum dot solution interacts with 0 μM of nimetazepam or flunitrazepam; a fluorescence emission spectrum under ultraviolet light irradiation at 300 nm (spectrum b) or a fluorescence emission spectrum under ultraviolet light irradiation at 365 nm (spectrum e) after the carbon quantum dot solution interacts with 100 μM of nimetazepam; and a fluorescence emission spectrum under ultraviolet light irradiation at 300 nm (spectrum c) or a fluorescence emission spectrum under ultraviolet light irradiation at 365 nm (spectrum f) after the carbon quantum dot solution interacts with 100 μM of flunitrazepam. The experimental results show that after the carbon quantum dot solution interacts with nimetazepam or flunitrazepam, the fluorescence intensity of the carbon quantum dots is significantly reduced. That is to say, nimetazepam or flunitrazepam causes significant fluorescence reduction of the carbon quantum dots.

Next, the standard concentration versus relative fluorescence intensity curves established under ultraviolet light irradiation at 300 nm (as shown in FIG. 3B) or 365 nm (as shown in FIG. 3C) after the carbon quantum dot solution interacts with different concentrations of nimetazepam (3.4 μM to 34 μM) or flunitrazepam (3.1 μM to 31.2 μM) and a standard concentration versus relative fluorescence quenching curve (embedded figure) are compared. Referring to FIG. 3A and FIG. 3B simultaneously, when the concentration of nimetazepam or flunitrazepam is increased, the fluorescence intensity of the carbon quantum dots is reduced. That is, the relative fluorescence quenching of carbon quantum dots (F0-F)/F0 (F0 is the fluorescence intensity value of the carbon quantum dots in the presence of 0 μM of nimetazepam or flunitrazepam, and F is the fluorescence intensity value of the carbon quantum dots in the presence of different concentrations of nimetazepam or flunitrazepam) has a positive correlation linear relationship with the standard concentration of nimetazepam or flunitrazepam (as shown in the embedded figures of FIG. 3B and FIG. 3C). In particular, the detection limits of nimetazepam under ultraviolet light irradiation at 300 nm and 365 nm are respectively about 0.77 μM (or 0.23 μg/ml) and 5.38 μM (or 1.59 μg/ml), and the detection limits of flunitrazepam under ultraviolet light irradiation at 300 nm and 365 nm are respectively about 0.79 μM (or 0.25 μg/ml) and 6.73 μM (or 2.11 μg/mL). From the above experiments, it may be confirmed that nimetazepam or flunitrazepam has a certain influence on the fluorescence intensity of the carbon quantum dots. Therefore, the detection kit 100 of the invention may use the carbon quantum dots as the fluorescent materials 160 to detect the presence of nimetazepam or flunitrazepam.

Experimental Example B

In this experimental example, the relative fluorescence quenching values after the carbon quantum dots are mixed with different abused drugs are examined to confirm the reducing effect thereof. First, the tested abused drugs included 1 mM heroin, 1 mM ketamine, 1 mM methamphetamine (MA), 1 mM cocaine, 1 mM 4-hydroxybutyric acid (GHB), 1 mM 4-chloroethcathinone, 100 μM alprazolam, 100 μM midazolam, 100 μM temazepam, 100 μM flunitrazepam (FM2), 100 μM nimetazepam (K5), 100 μM nitrazepam, and 100 μM clonazepam. Each of the above abused drug solutions were separately added to the reaction container of the reaction kit to allow the abused drugs to interact with the carbon quantum dots in the inspection solution, and testing was performed under ultraviolet light irradiation at 300 nm and 365 nm. Then, the relative fluorescence quenching (F0-F)/F0 of the carbon quantum dots thereof was calculated based on the detected fluorescence intensity, and the experimental results are shown in FIGS. 4A and 4B.

Figure 4A:
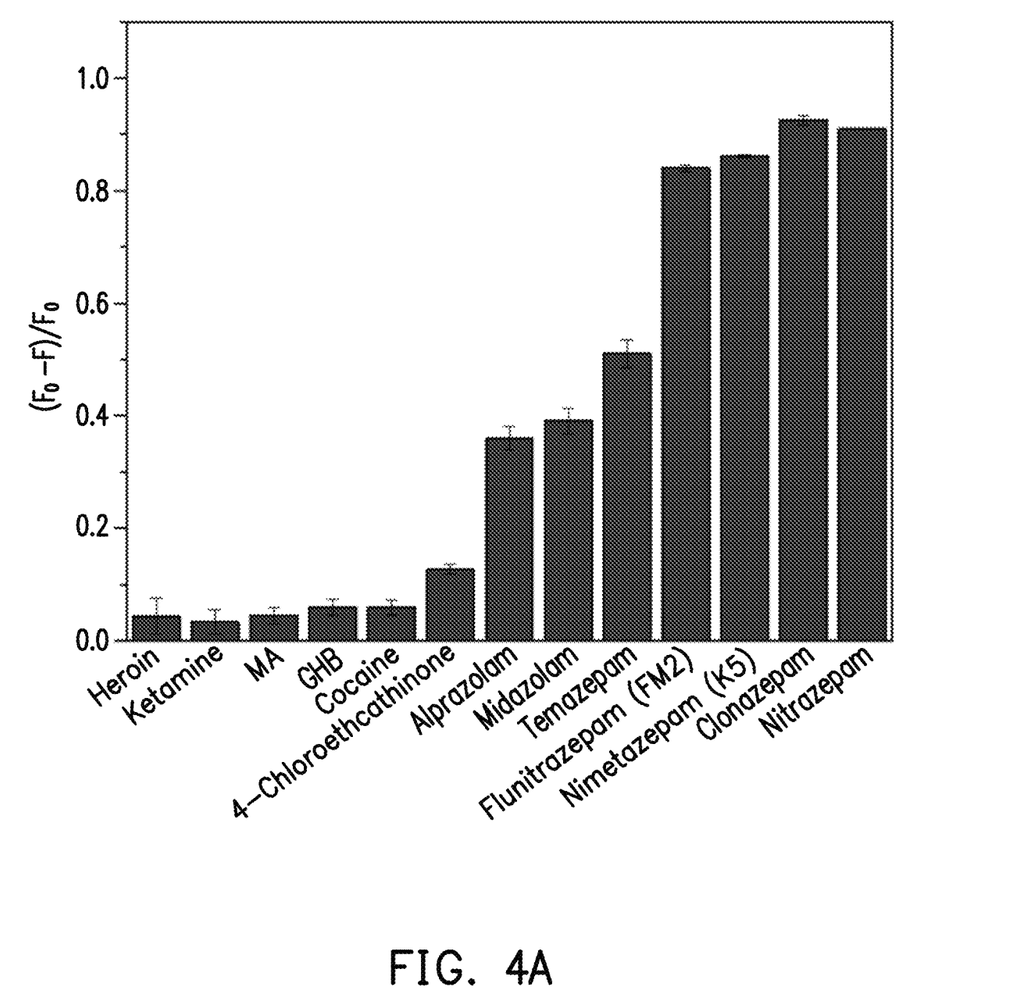
FIG. 4A shows a graph of fluorescence quenching under ultraviolet light irradiation at 300 nm after carbon quantum dots are mixed with different abused drugs.
Figure 4B:
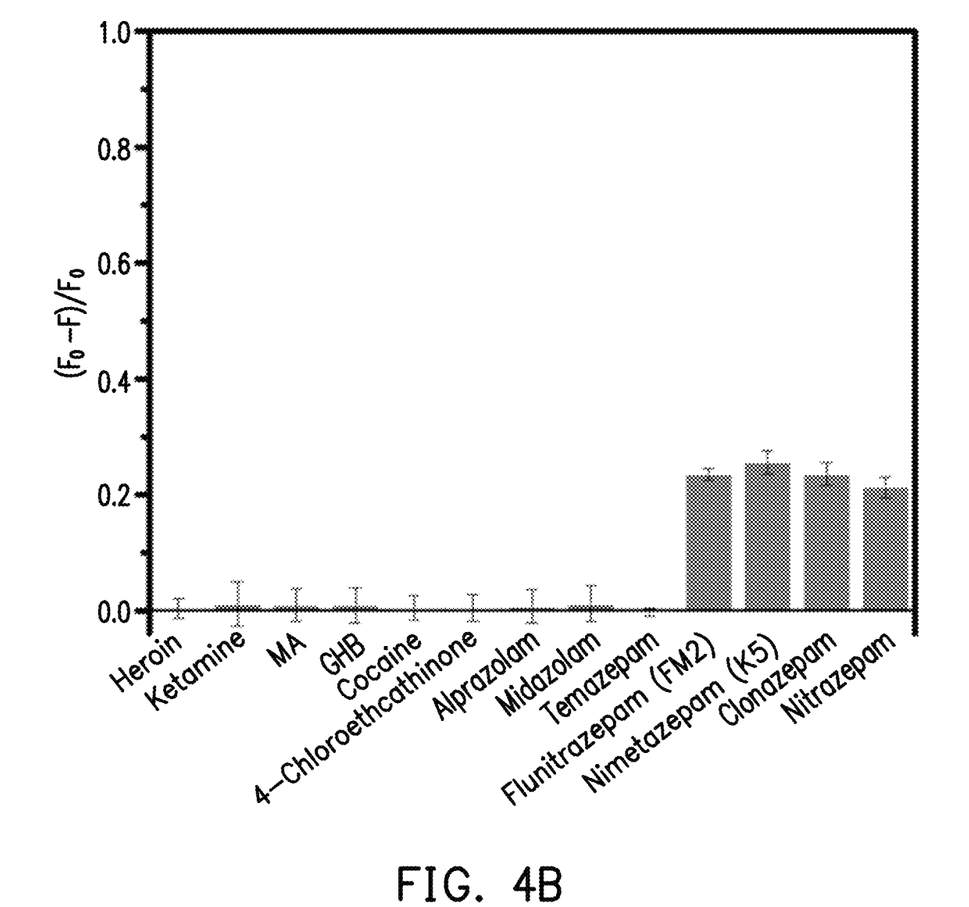
FIG. 4B shows a graph of fluorescence quenching under ultraviolet light irradiation at 365 nm after carbon quantum dots are mixed with different abused drugs.

FIG. 4A shows a graph of fluorescence quenching under ultraviolet light irradiation at 300 nm after carbon quantum dots are mixed with different abused drugs. FIG. 4B shows a graph of fluorescence quenching under ultraviolet light irradiation at 365 nm after carbon quantum dots are mixed with different abused drugs. Referring to FIG. 4A and FIG. 4B simultaneously, the relative fluorescence quenching of flunitrazepam, nimetazepam, clonazepam and nitrazepam under ultraviolet light irradiation at 300 nm or 365 nm are both the highest. That is, after flunitrazepam, nimetazepam, clonazepam or nitrazepam is mixed with inspection solution, it reacts with the carbon quantum dots in the inspection solution, thereby reducing the fluorescence intensity emitted by the carbon quantum dots. Conversely, since heroin, ketamine, MA, cocaine, GHB, and 4-chloroethcathinone do not interact with the carbon quantum dots, they do not significantly affect the fluorescence intensity of the carbon quantum dots. That is, the effect of the fluorescence quenching is not high.

Experimental Example C

Figure 5A:
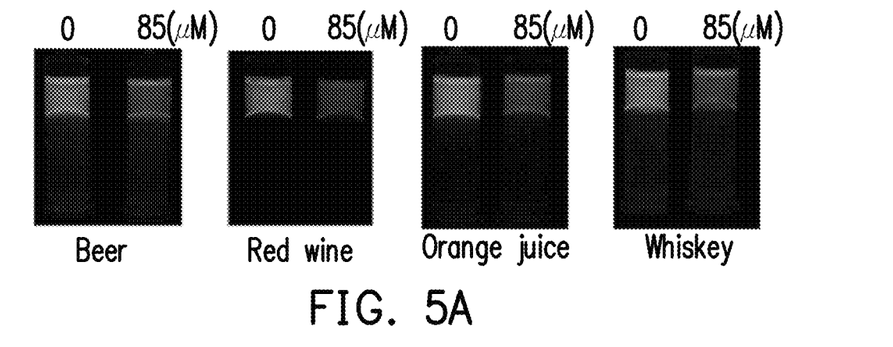
FIG. 5A to FIG. 5B are changes in fluorescence intensity after the detection kit of an embodiment of the invention interacts with nimetazepam in different test liquids.
Figure 5B:
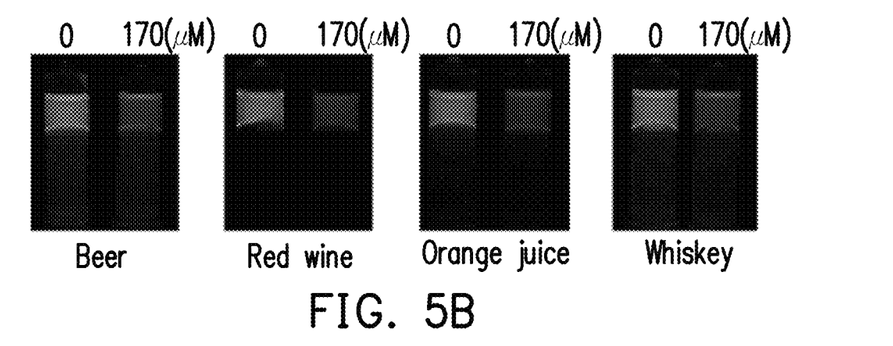

In this experimental example, the change in fluorescence intensity after the carbon quantum dots interact with nimetazepam (or flunitrazepam) disposed in different test liquids is examined to confirm the reducing effect thereof. First, the test liquids included beer, red wine, orange juice, and whiskey. Next, the changes in fluorescence intensity of different concentrations of nimetazepam (0, 85, 170 μM) in beer, red wine, orange juice, and whiskey were compared, as shown in FIG. 5A and FIG. 5B. The changes in fluorescence intensity of different concentrations of flunitrazepam (0, 32, 64 μM) in beer, red wine, orange juice, and whiskey were compared, as shown in FIG. 5C and FIG. 5D.

FIG. 5A to FIG. 5B are changes in fluorescence intensity after the detection kit of an embodiment of the invention interacts with nimetazepam in different test liquids. FIG. 5C to FIG. 5D are changes in fluorescence intensity after the detection kit of an embodiment of the invention interacts with flunitrazepam in different test liquids. Referring first to FIG. 5A, compared to 0 μM of nimetazepam, after 85 μM of nimetazepam in beer, red wine, orange juice, and whiskey interacts with the carbon quantum dots, under ultraviolet light irradiation at 365 nm, the fluorescence intensities of the carbon quantum dots are all significantly reduced. Similarly, referring to FIG. 5B, compared to 0 μM of nimetazepam, after 170 μM of nimetazepam in beer, red wine, orange juice, or whiskey interacts with the carbon quantum dots, under ultraviolet light irradiation at 365 nm, the fluorescence intensities of the carbon quantum dots are also significantly reduced.

Figure 5C:
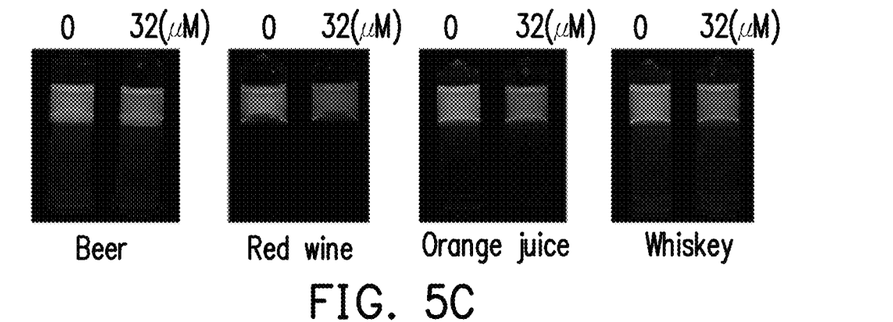
FIG. 5C to FIG. 5D are changes in fluorescence intensity after the detection kit of an embodiment of the invention interacts with flunitrazepam in different test liquids.
Figure 5D:
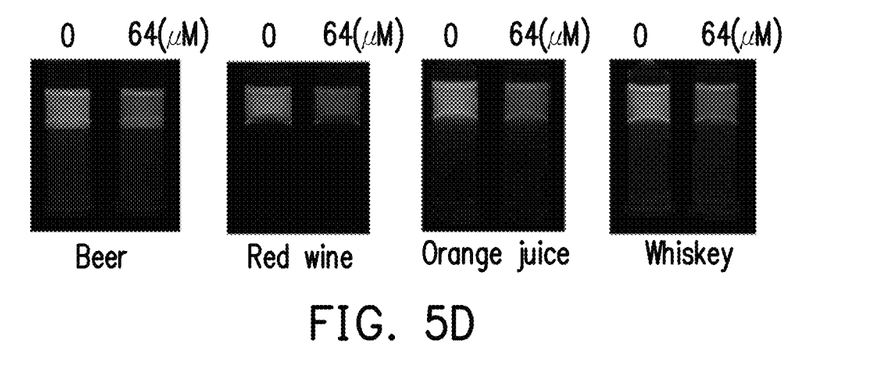

In addition, referring to FIG. 5C and FIG. 5D simultaneously, compared to 0 μM flunitrazepam, after 32 μM flunitrazepam (or 64 μM flunitrazepam) in beer, red wine, orange juice, or whiskey interacts with the carbon quantum dots, under ultraviolet light irradiation at 365 nm, the fluorescence intensity of the carbon quantum dots is also significantly reduced.

Based on the above, in the detection kit and the method for detecting abused drugs of the invention, the detection kit includes a reaction container, and a inspection solution composed of a hydrophobic solvent, and a plurality of fluorescent materials. In particular, the hydrophobic solvent is disposed in the reaction container and the fluorescent materials are dispersed in the hydrophobic solvent. Next, the test liquid is added to the reaction container and thoroughly mixed with the inspection solution and allowed to stand. Then, after the test liquid is thoroughly mixed and reacted with theinspection solution, the reducing condition of the fluorescence of the fluorescent materials in the hydrophobic solvent may be determined under ultraviolet light source irradiation to confirm whether the test liquid has abused drugs. Via this design, the detection kit and the method for detecting abused drugs of the invention have advantages such as simple manufacture, low cost, high stability, and easy storage.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A detection kit for detecting a target compound, comprising:
   a reaction container;
   an inspection solution composed of a hydrophobic solvent disposed in the reaction container; and
   a plurality of fluorescent materials dispersed in the inspection solution, wherein the fluorescent materials emit a blue fluorescence, and after the fluorescent materials interact with the target compound, an intensity of the blue fluorescence emitted by the fluorescent materials is decreasing,
   wherein the fluorescent materials are carbon quantum dots, the carbon quantum dots are synthesized from D-phenylalanine, and a fluorescence emission peak of the carbon quantum dots under ultraviolet light irradiation is at 360 mm to 460 mm,
   wherein the target compound comprises nimetazepam, flunitrazepam, clonazepam, nitrazepam, and nitro-substituted benzodiazepine.

2. The detection kit of claim 1, wherein the hydrophobic solvent comprises toluene, benzene, xylene, ethyl acetate, dichloromethane, or trichloromethane.

3. The detection kit of claim 1, wherein the fluorescent materials emit the blue fluorescence after being excited by an ultraviolet light, and after the fluorescent materials interact with the target compound, the fluorescence intensity emitted by the fluorescent materials is reduced.

4. A method for detecting abused drugs, comprising:
   providing a detection kit, comprising:
      a reaction container;
      an inspection solution composed of a hydrophobic solvent disposed in the reaction container; and
      a plurality of fluorescent materials dispersed in the inspection solution, wherein the fluorescent materials emit a blue fluorescence, and after the fluorescent materials interact with the target compound, an intensity of the blue fluorescence emitted by the fluorescent materials is decreasing;

adding a test liquid to the reaction container of the detection kit;

thoroughly mixing the test liquid with the inspection solution and allowing to stand;

irradiating with an ultraviolet light source after the test liquid is thoroughly mixed and reacted with the inspection solution;

determining, under irradiation by the ultraviolet light source, a reducing condition of a fluorescence intensity of the fluorescent materials in the inspection solution to confirm whether the test liquid has an abused drug, and confirming a concentration of the abused drug in the test liquid according to the reducing condition, wherein the fluorescent materials are carbon quantum dots, the carbon quantum dots are synthesized from D-phenylalanine, and a fluorescence emission peak of the carbon quantum dots under ultraviolet light irradiation is at 360 mm to 460 mm, wherein the abused drug comprises nimetazepam, flunitrazepam, clonazepam, nitrazepam, and nitro-substituted benzodiazepine.

5. The method for detecting the abused drugs of claim 4, further comprising:

slowly adding the test liquid to the inspection solution when the test liquid is added to the reaction container of the detection kit; or evenly shaking the reaction container up and down after the test liquid is added to the reaction container of the detection kit to increase an interaction between the abused drug in the test liquid and the fluorescent materials in the inspection solution wherein when the test liquid has the abused drug, the abused drug in the test liquid causes a blue fluorescence of the fluorescent materials in the inspection solution to be reduced.

6. The method for detecting the abused drugs according to claim 5, wherein the method for confirming the concentration of the abused drug in the test liquid according to the reducing condition comprises:

providing a series of the abused drug of a known concentration in the reaction container of the detection kit;

irradiating with an ultraviolet light source after the abused drug interacts with the fluorescent materials in the inspection solution;

determining a fluorescence intensity of the abused drug at each concentration to establish a standard concentration versus relative fluorescence quenching curve; and determining the reducing condition based on the standard concentration versus relative fluorescence quenching curve to confirm the concentration of the abused drug in the test liquid.

* * * * *